United States Patent [19] [11] 4,057,973
Murphy et al. [45] Nov. 15, 1977

[54] CONSTANT BOILING MIXTURES OF 1-CHLORO-2,2,2-TRIFLUOROETHANE AND 2-CHLOROHEPTAFLUOROPROPANE

[75] Inventors: Kevin P. Murphy, Orchard Park; Richard F. Stahl, Hamburg; Sabatino R. Orfeo, Orchard Park, all of N.Y.

[73] Assignee: Allied Chemical Corporation, Morris Township, N.J.

[21] Appl. No.: 753,063

[22] Filed: Dec. 21, 1976

[51] Int. Cl.$^2$ .......................... C09K 5/04; F25B 9/00
[52] U.S. Cl. ........................................ 62/114; 252/66; 252/67; 252/78.1; 252/305; 252/364; 252/DIG. 9
[58] Field of Search ............. 252/DIG. 9, 67, 66, 252/162, 305, 364, 78.1; 62/114

[56] References Cited

U.S. PATENT DOCUMENTS

| | | | |
|---|---|---|---|
| 3,583,921 | 6/1971 | Healy et al. | 252/90 |
| 3,733,273 | 5/1973 | Munro | 252/DIG. 9 X |
| 3,770,838 | 11/1973 | Dear et al. | 260/653 |
| 4,024,086 | 5/1977 | Hutchinson | 252/162 |

OTHER PUBLICATIONS

Stiel et al., "Optimum Properties of Working Fluids for Solar Powered Heat Pumps", Rec. Intersoc. Energy Convers. Eng. Conf., 10th, 1975, 171–177; C.A. 84:76778q.

*Primary Examiner*—Harris A. Pitlick
*Attorney, Agent, or Firm*—Jay P. Friedenson

[57] ABSTRACT

Constant boiling mixtures of 1-chloro-2,2,2-trifluoroethane and 2-chloroheptafluoropropane are useful as refrigerants, heat transfer media, gaseous dielectrics, expansion agents, aerosol propellants, working fluids in a power cycle and solvents.

4 Claims, No Drawings

CONSTANT BOILING MIXTURES OF 1-CHLORO-2,2,2-TRIFLUOROETHANE AND 2-CHLOROHEPTAFLUOROPROPANE

BACKGROUND OF THE INVENTION

This invention relates to mixtures of fluorinated hydrocarbons and more particularly to constant boiling fluorocarbon mixtures which comprise 1-chloro-2,2,2-trifluoroethane and 2-chloroheptafluoropropane. Such mixtures are especially useful as compression refrigerants, particularly in systems using centrifugal or rotary compressors.

The refrigerant capacity per volume pumped of a refrigerant is largely a function of boiling point, the lower boiling refrigerants generally offering the greater capacity at a given evaporator temperature. This factor to a great extent influences the design of refrigeration equipment and affects capacity, power requirements, size and cost of the unit. Another important factor related to boiling point of the refrigerant is minimum cooling temperature desired during the refrigeration cycle, the lower boiling refrigerants being used to achieve the lower refrigeration temperatures. For these reasons, a large number of refrigerants of different boiling temperature and capacity are required to permit flexibility of design and the art is continually faced with the problem of providing new refrigerants as the need arises for new capacities and types of installations.

The lower aliphatic hydrocarbons when substituted by fluorine and chlorine are well-known to have potential as refrigerants. Many of these fluoro-chloro hydrocarbons exhibit certain desired properties including lower toxicity and nonflammability which have resulted in extensive use of such compounds in a large number of refrigeration applications. Trichlorofluoromethane and dichlorodifluoromethane are two of the most commonly available chlorine-fluorine hydrocarbon refrigerants available today. There is a recognized need for refrigerants with boiling point temperatures between the relatively high boiling point temperature of trichlorofluoromethane, plus 23.78° C. at atmospheric pressure, and the relatively low boiling point temperature of dichlorodifluoromethane, minus 29.8° C. at atmospheric pressure, in order to have available refrigerants of good performance in varying capacities.

Several fluoro-chloro hydrocarbons have boiling points in this range but suffer from other deficiencies such as flammability, poor stability or poor thermodynamic performance. Some examples of these types of refrigerants are tetrafluorodichloroethane, fluorodichloromethane, difluorochloroethane and fluorochloromethane.

It would also be possible to achieve the desired boiling point by mixing two refrigerants with boiling points above and below the desired one. In this case, for example, mixtures of trichlorofluoromethane and dichlorodifluoromethane could be used. It is well known, however, that simple mixtures create problems in design and operation because of segregation of the components in the liquid and vapor phases. This problem is particularly troublesome in systems using centrifugal compression because of the large quantities of liquid usually found in the evaporator.

To avoid such segregation problems, the art is continually searching for new azeotrophic or constant boiling blends such as the constant boiling fluorocarbon blends disclosed in U.S. Pat. Nos. 3,607,755; 3,470,101; 3,640,869; 3,505,232; 3,634,255 and *Soap and Chemicals Specialties,* August, 1964.

An object of the present invention is to provide new mixtures with boiling points between that of trichlorofluoromethane and dichlorodifluoroethane suitable for use as refrigerants.

More particularly, it is an object of the present invention to provide refrigerant systems with a capacity between the refrigeration capacity of trichlorofluoromethane and dichlorodifluoroethane and which are useful as compression refrigerants, particularly in systems using a centrifugal or rotary compressor.

Another object is to provide new, low boiling azeotropic or constant boiling mixtures which are useful in producing refrigeration in those systems in which cooling is achieved by evaporation in the vicinity of the body to be cooled and in which because of the nature of the system, the problem of segregation is critical.

DESCRIPTION OF THE INVENTION

In accordance with the present invention, azeotropic or constant boiling mixtures have been discovered which consist essentially of about 29 mole percent of 1-chloro-2,2,2-trifluoroethane and about 71 mole percent of 2-chloroheptafluoropropane at 20.0° C. For the purpose of this discussion, by azeotropic or constant boiling is intended to mean also essentially azeotropic or essentially constant boiling. In other words, included within the meaning of these terms are not only the true azeotrope described above at 20.0° C, but also other compositions containing the same components in different proportions which are true azeotropes at other temperatures and pressures, as well as those equivalent compositions which are part of the same azeotropic system and are azeotrope-like in their properties. As is well recognized in this art, there is a range of compositions containing the same components as the azeotrope, which, not only will exhibit essentially equivalent properties for refrigeration and other applications, but which will exhibit essentially equivalent properties to the true azeotropic composition in terms of constant boiling characteristics or tendency not to fractionate upon boiling.

The novel azeotropic composition of the invention has a boiling point of about −5° C at atmospheric pressure (760 mm Hg.). 1-Chloro-2,2,2-trifluoroethane has a boiling point of about 6.1° C at atmospheric pressure and 2-chloroheptafluoropropane has a boiling point of about −2.6° C. at atmospheric pressure. The azeotropic mixtures exhibit marked reduction in boiling point temperature as compared with the boiling temperatures of the components. From the properties of the components alone, the marked reduction in the boiling point temperature and azeotropic characteristics in the mixtures are not expected.

The novel azeotropic mixtures provide substantially increased refrigeration capacity over the components and represent new refrigeration mixtures especially useful in systems using centrifugal and rotary compressors. The use of the azeotropic mixtures eliminate the problem of segregation and handling in the operation of the system because of the behavior of azeotropic mixtures essentially as a single component. The novel azeotropic mixtures are substantially non-flammable.

EXAMPLE

A phase study was made on 1-chloro-2,2,2-trifluoromethane (b.p. 6.1° C/760 mm) and 22-chloroheptafluoropropane (b.p.— 2.6° C./760 mm) wherein the composition was varied and the vapor pressures were measured at a temperature of 20.0° C. An azeotropic composition at 20° C was obtained at the maximum pressure and was as follows:

1-chloro-2,2,2-trifluoroethane 29 mole %
2-chloroheptafluoropropane 71 mole %

The lower boiling point of the azeotrope compared to its components, affords increased refrigerating capacity over both components and a new level of refrigerating capacity.

Additives such as lubricants, corrosion inhibiters and others may be added to the novel compositions of the invention for a variety of purposes provided they do not have an adverse influence on the compositions for their intended applications.

In addition to refrigerant applications, the novel constant compositions of the invention are also useful as heat transfer media, gaseous dielectrics, expansion agents such as for polyolefins and polyurethanes, working fluids in power cycles, solvents and as aerosol propellants which may be particularly environmentally acceptable.

We claim:
1. Constant boiling mixtures consisting essentially of about 29 mole % of 1-chloro-2,2,2-trifluoroethane and about 71 mole % of 2-chloroheptafluoropropane.
2. Constant boiling mixtures according to claim 1 which boil at about −5° C. at 760 mm.
3. The process of producing refrigeration which comprises condensing a constant boiling mixture as described in claim 1 and thereafter evaporating said mixture in the vicinity of a body to be cooled.
4. The process of producing refrigeration according to claim 3 in which the constant boiling mixture condensed and evaporated is as defined in claim 2.

* * * * *